United States Patent
Maekawa et al.

(10) Patent No.: US 12,240,378 B2
(45) Date of Patent: Mar. 4, 2025

(54) LIGHT EMITTING DEVICE

(71) Applicant: TOYOTA BOSHOKU KABUSHIKI KAISHA, Aichi-ken (JP)

(72) Inventors: Motoki Maekawa, Aichi-ken (JP); Ryosuke Usami, Aichi-ken (JP); Masahiro Irie, Aichi-ken (JP); Yohei Ishizu, Aichi-ken (JP); Mitsutaka Sakoh, Aichi-ken (JP)

(73) Assignee: TOYOTA BOSHOKU KABUSHIKI KAISHA, Aichi-Ken (JP)

( * ) Notice: Subject to any disclaimer, the term of this patent is extended or adjusted under 35 U.S.C. 154(b) by 313 days.

(21) Appl. No.: 17/588,593

(22) Filed: Jan. 31, 2022

(65) Prior Publication Data

US 2022/0242235 A1  Aug. 4, 2022

(30) Foreign Application Priority Data

Feb. 3, 2021 (JP) ................................. 2021-015795

(51) Int. Cl.
*B60Q 3/51* (2017.01)
*B60Q 3/59* (2017.01)
(Continued)

(52) U.S. Cl.
CPC ................ *B60Q 3/70* (2017.02); *B60Q 3/51* (2017.02); *B60Q 3/59* (2017.02); *H01L 33/64* (2013.01)

(58) Field of Classification Search
CPC ... B60Q 3/51; B60Q 3/59; B60Q 3/70; B60Q 3/68; H01L 33/64; H01L 33/648;
(Continued)

(56) References Cited

U.S. PATENT DOCUMENTS 6,787,782 B1 * 9/2004 Krosney .................. A61L 9/20
250/435
10,139,096 B2  11/2018 Kobayashi
(Continued)

FOREIGN PATENT DOCUMENTS

CN        106931356        7/2017
CN        211797808 U      10/2020
(Continued)

OTHER PUBLICATIONS

China Office Action issued in China Patent Application No. 202210112532.9, dated May 7, 2023, together with English translation thereof.
(Continued)

*Primary Examiner* — Kiet T Nguyen
(74) *Attorney, Agent, or Firm* — Greenblum & Bernstein, P.L.C.

(57) ABSTRACT

A light emitting device to be mounted on a mount surface of a vehicular compartment includes a housing including a first section having an air intake hole and a second section having an air discharge hole, a cooling fan device arranged in the first section, and a light emitter arranged in the second section. The housing further includes a discharge cavity having the discharge hole. The light emitter and the cooling fan device are arranged in a first arrangement direction laterally along the mount surface. The light emitter includes a board member and a light emitting element. The board member has a first surface that is opposite the mount surface and a second surface that is an opposite surface of the first surface and on which the light emitting element is mounted. The first surface of the board member is defined as a portion of the discharge cavity.

5 Claims, 6 Drawing Sheets

(51) Int. Cl.
  *B60Q 3/70* (2017.01)
  *H01L 33/64* (2010.01)
(58) Field of Classification Search
  CPC .......... A61L 2/10; A61L 2/26; A61L 2202/11;
           A61L 2202/25; H05K 7/20145; H05K
                         7/20172; Y02E 60/14
  USPC ........................................................ 362/488
  See application file for complete search history.

(56) References Cited

U.S. PATENT DOCUMENTS

| | | | |
|---|---|---|---|
| 2012/0051073 A1* | 3/2012 | Salter ................. | B60R 13/0212 |
| | | | 29/428 |
| 2017/0191650 A1 | 7/2017 | Kobayashi | |
| 2020/0197550 A1 | 6/2020 | Barron et al. | |

FOREIGN PATENT DOCUMENTS

| | | |
|---|---|---|
| JP | 2006-021098 | 1/2006 |
| JP | 2012-254673 | 12/2012 |
| WO | 2020/132244 | 6/2020 |

OTHER PUBLICATIONS

Japan Office Action issued in Japan Patent Application No. 2022-11438, dated Nov. 19, 2024, together with English translation thereof.

* cited by examiner

LIGHT EMITTING DEVICE

CROSS REFERENCE TO RELATED APPLICATION

This application claims priority from Japanese Patent Application No. 2021-15795 filed on Feb. 3, 2021. The entire contents of the priority application are incorporated herein by reference.

TECHNICAL FIELD

The technology described herein relates to a light emitting device to be mounted in a vehicle.

BACKGROUND

A light emitter that is to be mounted in a vehicle and configured to emit light includes a photocatalyst-containing member, an irradiating means, a heat storage, and an air sending means that are disposed on top of each other. The irradiating means is for irradiating the photocatalyst-containing member with ultraviolet-containing light. The heat storage is for storing heat and supplying the heat to the photocatalyst of the photocatalyst-containing member. The air sending means is for sending air to the photocatalyst-containing member. The air is transferred from the air sending means to the irradiating means and the photocatalyst containing member through the heat storage.

In such a light emitter, the heat generated by the irradiating means is cooled by the air sending means. In the light emitter, the irradiating means and the air sending means are disposed to overlap each other while having the heat storage therebetween. This increases the dimension of the light emitter measuring in the overlapping direction. When such a light emitter is mounted on a ceiling of a vehicle such that the air sending means is on the ceiling, the light emitter projects from the ceiling with the increased dimension of the light emitter. This requires the vehicle to have a sufficient inner space from the ceiling; however, it is not easy to keep such a space in the vehicle. Even if such a space can be provided in the vehicle and the light emitter is mounted on the ceiling, a passenger may hit his or her head with the light emitter that projects from the ceiling with the increased dimension. Therefore, the light emitter is required to reduce its projection dimension when being mounted on a mount surface such as the ceiling of a vehicle and a light emitter has been demanded to be thinner.

Removing virus has been demanded in a vehicle every time the vehicle is used. It has been known that among the ultraviolet light, deep ultraviolet light having a short wavelength (100 nm to 280 nm) has an effect of removing virus and the irradiation of deep ultraviolet light may be used for vehicles for removing virus. A deep ultraviolet light emitting device outputs higher energy compared to a light emitting device emitting visible light and a light emitting device emitting ultraviolet light having long wavelength. Therefore, cooling efficiency needs to be improved in the light emitting device emitting deep ultraviolet light.

SUMMARY

The technology described herein was made in view of the foregoing circumstances. An object is to provide a light emitting device that is thin and has good cooling efficiency.

The present disclosure is related to a light emitting device that is to be mounted on a mount surface of a vehicular compartment. The light emitting device includes a housing having a box shape including a first section and a second section, a cooling fan device arranged in the first section, and a light emitter arranged in the second section. The first section has an air intake hole and the second section has an air discharge hole and the housing includes a discharge cavity having the discharge hole. The light emitter is arranged next to the cooling fan device in a first arrangement direction and laterally along the mount surface. The light emitter includes a board member and a first light emitting element. The board member has a first surface that is opposite the mount surface of the vehicular compartment and a second surface that is an opposite surface of the first surface. The first surface is defined as a portion of the discharge cavity. The first light emitting element is mounted on the second surface of the board member.

DETAILED DESCRIPTION

A deep ultraviolet light emitting device 10 according to one embodiment will be described in detail with reference to FIGS. 1 to 7. An X-axis, a Y-axis, and a Z-axis illustrated in each drawing represent respective directions. An X-axis direction, a Y-axis direction, and a Z-axis direction represent a right direction, a front direction, and an upper direction, respectively. Regarding components having the same configuration, some of the components may be indicated by reference signs and others may not be indicated by the reference signs.

Figure 1:
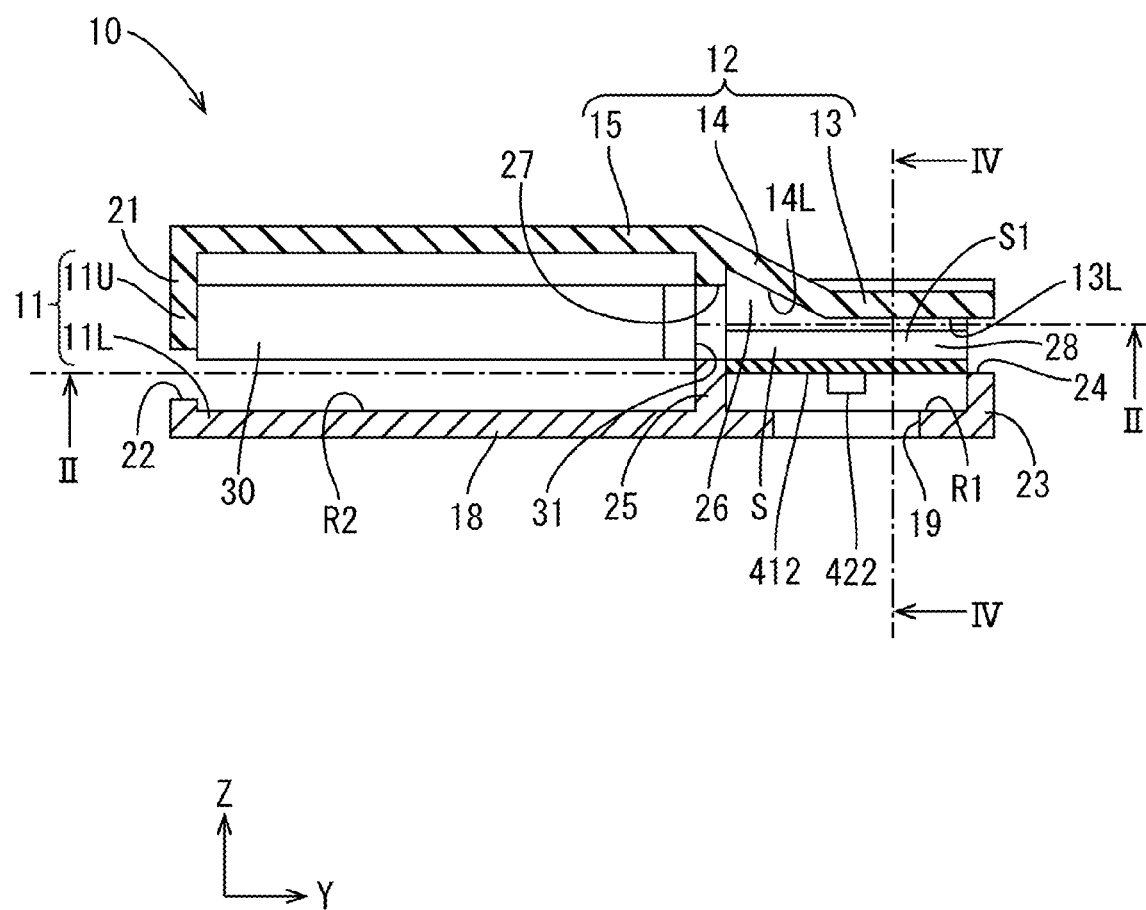
FIG. 1 is a cross-sectional view of a deep ultraviolet light emitting device along line I-I in FIG. 3.
Figure 3:
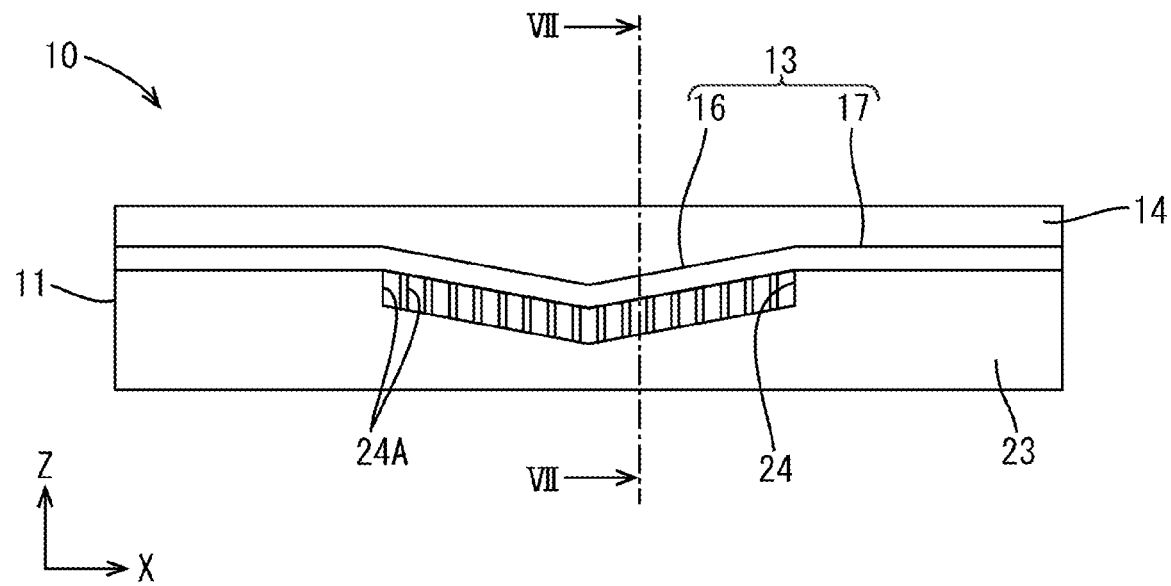
FIG. 3 is an elevation view of the deep ultraviolet light emitting device.
Figure 4:
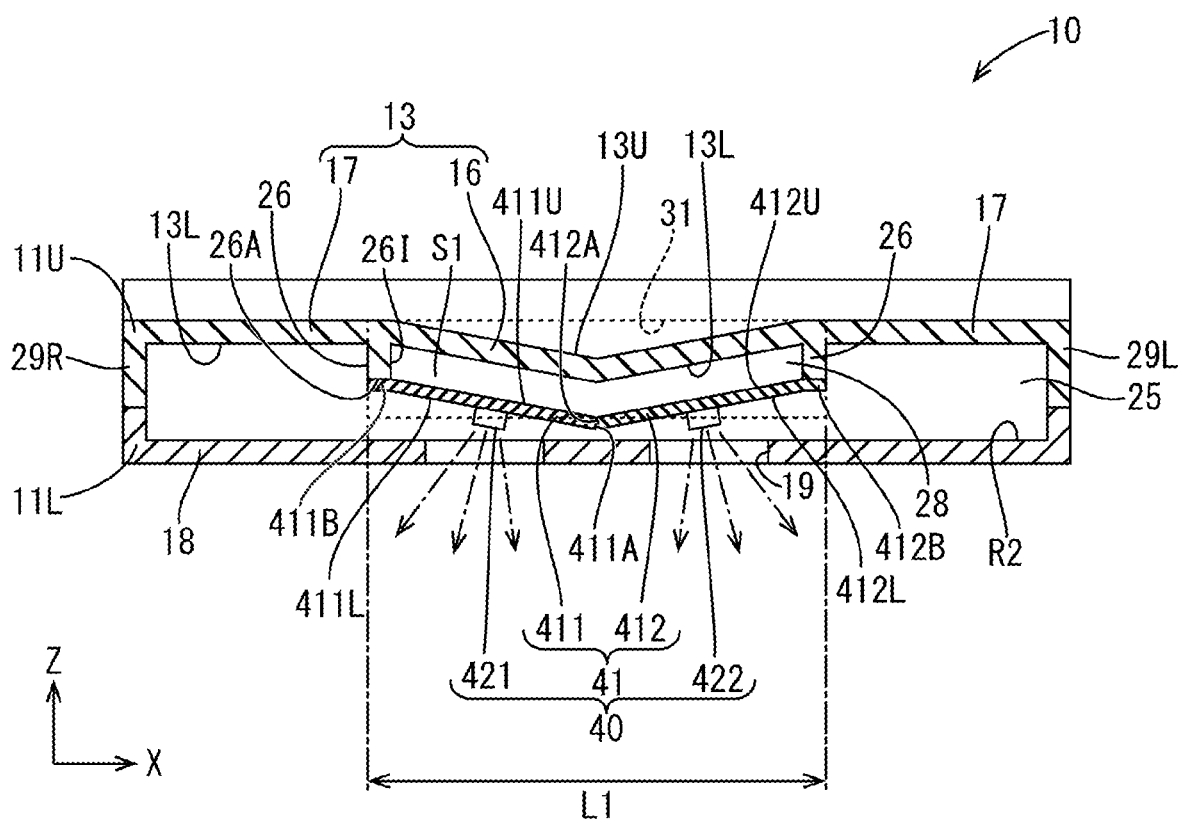
FIG. 4 is a cross-sectional view of the deep ultraviolet light emitting device along line IV-IV.

As illustrated in FIGS. 1 and 3, the deep ultraviolet light emitting device 10 includes a housing 11 that has a flat box shape as a whole. The housing 11 includes a top wall 12, a bottom wall 18 that is opposite the top wall 12, a rear wall 21 (a first wall), a front wall 23 (a second wall), a right side wall 29R (a third wall), and a left side wall 29L (a fourth wall). The rear wall 21 and the front wall 23 are opposite each other in a front-rear direction (the Y-axis direction) and each of the rear wall 21 and the front wall 23 connects the top wall 12 and the bottom wall 18. The left side wall 29L and the right side wall 29R are opposite each other in a right-left direction (the X-axis direction). Each of the left side wall 29L and the right side wall 29R connects the top wall 12 and the bottom wall 18 and connects the rear wall 21 and the front wall 23. As illustrated in FIGS. 1 and 4, the housing 11 includes an upper member 11U and a lower member 11L. The upper member 11U includes the top wall 12, the rear wall 21, a section of the left side wall 29L, and a section of the right side wall 29R. The lower member 11L includes the bottom wall 18, the front wall 23, another section of the left side wall 29L, and another section of the right side wall 29R. The rear wall 21 includes an intake hole 22 and the front wall 23 includes a discharge hole 24.

The top wall 12 includes a first top wall section 15 that is close to the rear wall 21, a second top wall section 13 that is close to the front wall 23, and a middle top wall section 14 that is between the first top wall section 15 and the second top wall section 13 and connects them. The second top wall section 13 is disposed lower than the first top wall section 15 and the middle top wall section 14 is tilted and extends downward from the first top wall section 15 to the second top wall section 13. The middle top wall section 14 is tilted at 35 degrees with respect to a horizontal direction. The bottom wall 18 includes holes 19 corresponding to LEDs, which will be described later. The bottom wall 18 may not include the holes 19 and may be made of transparent or semitransparent material through which the deep ultraviolet light passes. An example of such material is quarts.

Figure 2:
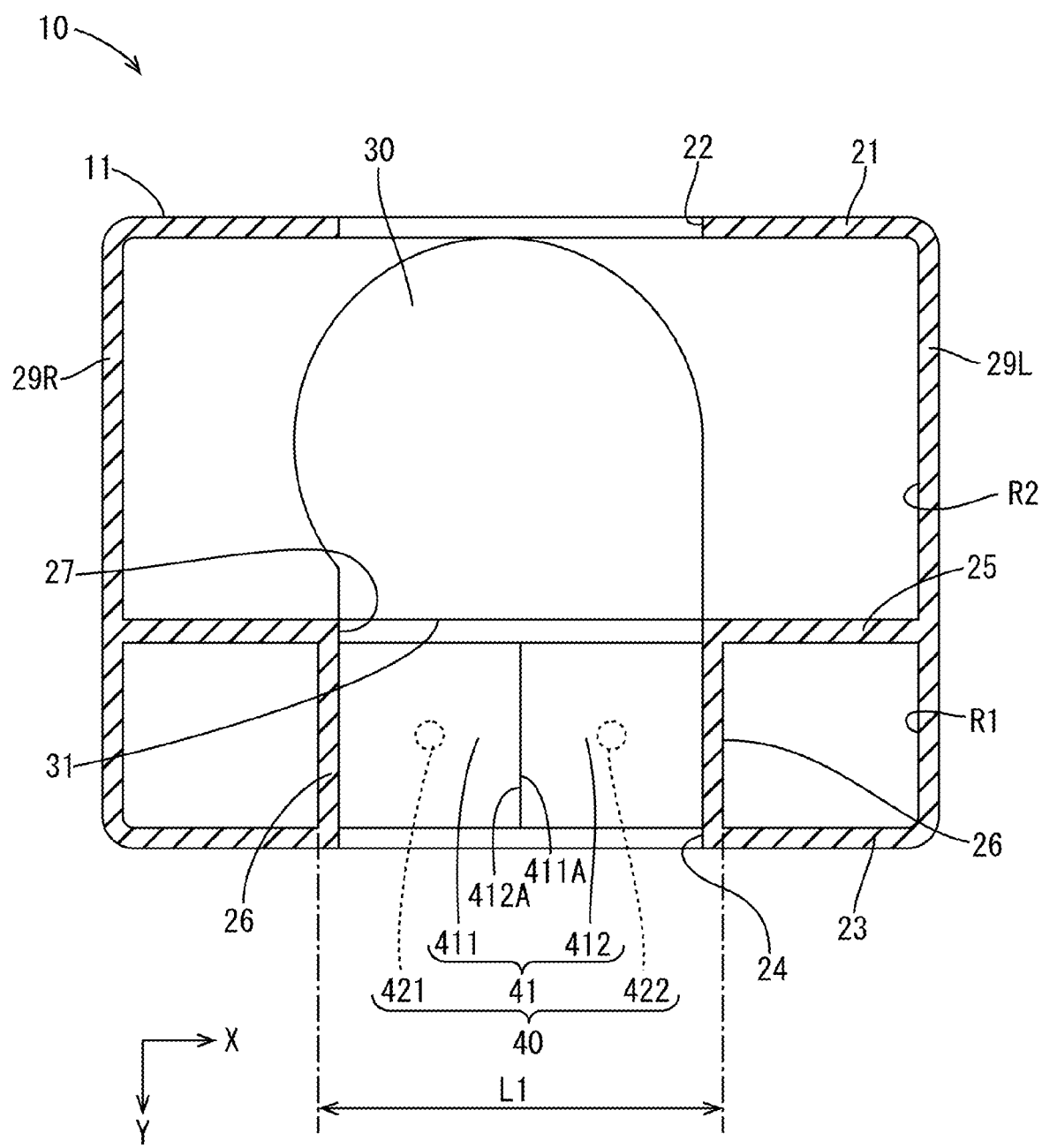
FIG. 2 is a cross-sectional view of the deep ultraviolet light emitting device along line II-II in FIG. 1.

As illustrated in FIGS. 1 and 2, the rear wall 21 includes the intake hole 22 that is through the rear wall 21 and the front wall 23 includes the discharge hole 24 that is through the front wall 23. Each of the rear wall 21 and the front wall 23 is a rectangular plate that extends from the left side wall 29L to the right side wall 29R. The rear wall 21 includes the intake hole 22 in a middle section thereof in a longitudinal direction of the rear wall 21. The intake hole 22 may extend from the left side wall 29L to the right side wall 29R in a lower section of the rear wall 21. The intake hole 22 and the discharge hole 24 extend in the longitudinal direction of the rear wall 21 and the front wall 23. The intake hole 22 and the discharge hole 24 have an elongated shape having two short side opening edges and upper and lower long opening edges. The intake hole 22 and the discharge hole 24 are divided into slits 24A such that foreign obstacles do not enter the housing 11. As illustrated in FIG. 3, the slits 24A are defined in the discharge hole 24. The slits are not described in FIGS. 1 and 2.

As illustrated in FIGS. 1 and 2, the housing 11 includes a dividing wall 25 between the rear wall 21 and the front wall 23. The dividing wall 25 is opposite and parallel to the rear wall 21 and the front wall 23. The dividing wall 25 extends from the top wall 12 to the bottom wall 18 and divides an inner space of the housing 11 into a front section R1 (a second section) and a rear section R2 (a first section). The dividing wall 25 extends from the right side wall 29R to the left side wall 29L. The front section R1 is defined by the dividing wall 25, the front wall 23, a front section of the left side wall 29L close to the front wall 23, a front section of the right side wall 29R close to the front wall 23, the second top wall section 13, the middle top wall section 14, and a front section of the bottom wall 18. The rear section R2 is defined by the dividing wall 25, the rear wall 21, a rear section of the left side wall 29L close to the rear wall 21, a rear section of the right side wall 29R close to the rear wall 21, the first top wall section 15, and a rear section of the bottom wall 18. The dividing wall 25 extends in a top-bottom direction from the top wall 12 to the bottom wall 18 and extends in the right-left direction (the X-axis direction) from the left side wall 29L to the right side wall 29R. The dividing wall 25 extends downward from a border between the first top wall section 15 and the middle top wall section 14. As illustrated in FIGS. 1 and 2, the dividing wall 25 includes a through hole 27 in a middle section with respect to the longitudinal direction of the dividing wall 25 (the right-left direction). The through hole 27 is an elongated hole extending in the longitudinal direction of the dividing wall 25. The front section R1 and the rear section R2 are communicated with each other through the through hole 27.

A cooling fan device 30 and a control circuit board are arranged in the rear section R2 of the housing 11. A light emitter 40 is arranged in the front section R1 of the housing 11.

The cooling fan device 30 has a flat circular columnar shape as a whole. The cooling fan device 30 is arranged in the rear section R2 such that upper and lower plate surfaces of a body member of the cooling fan device 30 face upward and downward, respectively. The cooling fan device 30 includes an inlet in a bottom plate member thereof and an outlet in a front side wall thereof. The cooling fan device 30 suctions air through the inlet and feeds the air into the rear section R2 through the outlet 31 and further feeds the air toward the through hole 27. The intake hole 22 of the housing 11 is positioned below a lower edge of the cooling fan device 30 when the cooling fan device 30 is arranged at a predefined position in the rear section R2 of the housing 11. The cooling fan device 30 is fixed to the rear wall 21 and may be fixed to the first top wall section 15 or the dividing wall 25 a with fixing member.

As illustrated in FIGS. 2 and 4, the light emitter 40 includes a board member 41 including a first board 411 (one example of a first board section) and a second board 412 (one example of a second board section), a first LED 421 (one example of a lighting element) mounted on a lower surface 411L of the first board 411, and a second LED 422 (one example of the lighting element) mounted on a lower surface 412L of the second board 412. Each of the first board 411 and the second board 412 is a flat board. As illustrated in FIGS. 1 and 4, the cooling fan device 30 that is flat and the board member 41 that is flat as a whole are arranged next to each other such that the plate surfaces thereof do not overlap.

The first LED 421 and the second LED 422 are deep-UV LEDs that emit deep-UV light having a short wavelength (100 nm to 280 nm) among various types of UV light. The wavelength range of the deep-UV light emitted by the first LED 421 and the second LED 422 is preferably from 200 nm to 280 nm. The first board 411 and the second board 412 may include visible light LEDs that emit visible light in addition to the first LED 421 and the second LED 422.

Figure 5:
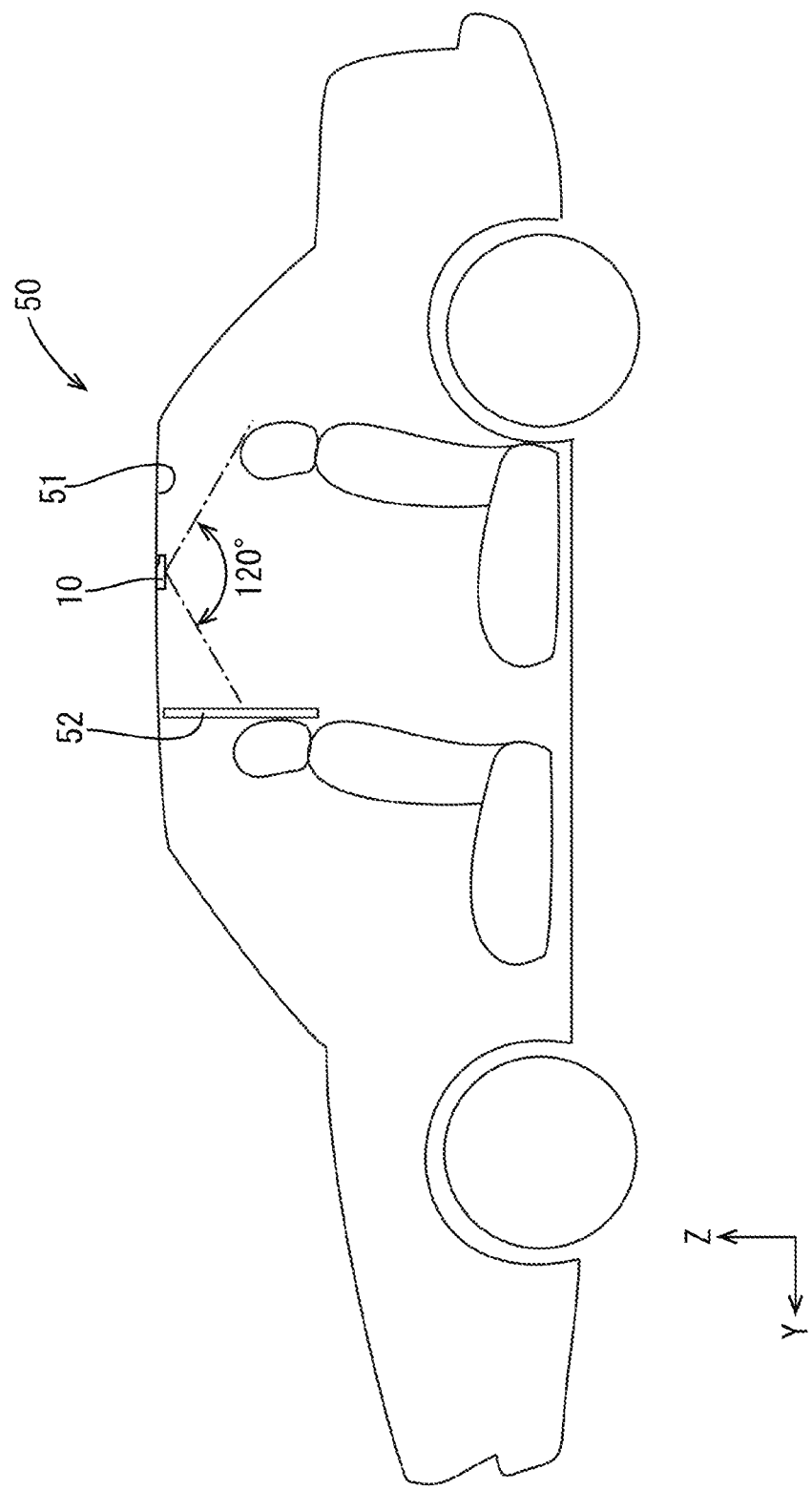
FIG. 5 is a side view of a vehicle compartment including the deep ultraviolet light emitting device.
Figure 6:
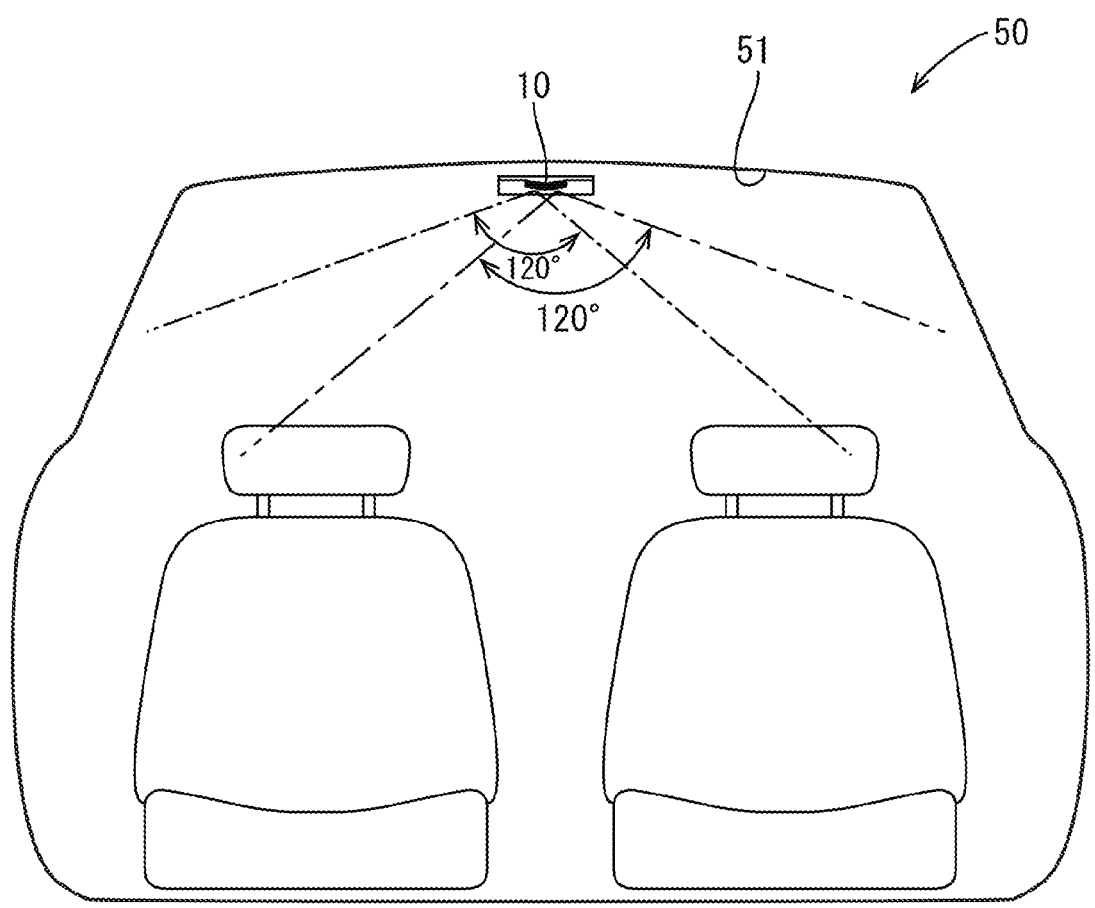
FIG. 6 is a front view of the vehicle compartment including the deep ultraviolet light emitting device.

The first LED 421 and the second LED 422 are mounted on the first board 411 and the second board 412 while mounting surfaces of the first LED 421 and the second LED 422 being on the first board 411 and the second board 412, respectively. The first LED 421 and the second LED 422 emit light through top surfaces that are opposite surfaces from the mounting surfaces and are top-surface light emission type LEDs. As illustrated in FIGS. 5 and 6, the angle of orientation of light emitted by the first LED 421 and the second LED 422 is 120 degrees around a vertical axis with respect to the top surface.

The first board 411 and the second board 412 are made of aluminum. As illustrated in FIG. 4, the board member 41 is made of aluminum and has a shallow V-shape. The first board 411 and the second board 412 are arranged next to each other in a board arrangement direction (the right-left direction, a second arrangement direction, a direction crossing an extending direction of a cavity 28). The first board 411 and the second board 412 are connected at a connection edge 411A of the first board 411 and a connection edge 412A of the second board 412 at an angle, as illustrated in FIG. 4. The board member 41 is angled at a middle section thereof. More specifically, each of the first board 411 and the second board 412 is tilted at 15 degrees with respect to the horizontal direction and extends downward toward the middle in the right-left direction. The first board 411 and the second board 412 form an angle of 150 degrees. According to such a configuration, the top surface of the first LED 421 faces downward and obliquely rightward (toward the right side wall 29R) and the top surface of the second LED 422 faces downward and obliquely leftward (toward the left side wall 29L). The board member 41 may be one plate member that is bent and includes a first board section and a second board section.

As illustrated in FIGS. 2 and 4, the board member 41 includes the first board 411 and the second board 412 that are arranged next to each other to form an angled shape and has an elongated shape extending in the board arrangement direction. The board member 41 has a width L1 measuring in the elongated direction (the right-left direction, the board arrangement direction). The width L1 is about a half of a width dimension of the housing 11 measuring in the right-left direction. The board member 41 including the first board 411 and the second board 412 has a length measuring in the front-rear direction (a direction perpendicular to the board arrangement direction) and the length of the board member 41 is equal to a dimension extending from the dividing wall 25 to the front wall 23 in the front-rear direction. A dimension of the front section R1 measuring in the front-rear direction is from the dividing wall 25 to the front wall 23. Therefore, as illustrated in FIGS. 1 and 2, the board member 41 is just fitted in the front section R1 of the housing 11 with respect to the front-rear direction. The discharge hole 24 has a width measuring in the longitudinal direction of the front wall 23 and the width dimension is almost same as or slightly greater than the width L1 of the board member 41 including the first board 411 and the second board 412. The width of the discharge hole 24 and the through hole 27 measuring in the right-left direction is about a half of the width of the housing 11 measuring in the right-left direction.

As illustrated in FIG. 4, the second top wall section 13 includes a recessed portion 16 and horizontal portions 17. The second top wall section 13 includes the recessed portion 16 in a middle thereof relative to the right-left direction and the recessed portion 16 includes two sloped portions that form a cross section of a shallow V-shape. The recessed portion 16 of the second top wall section 13 is bent such that a lower surface 13L of the recessed portion 16 extends parallel to an upper surface 411U of the first board 411 and an upper surface 412U of the second board 412. An upper surface 13U of the recessed portion 16 extends similarly to the lower surface 13L. The horizontal portions 17 are on the right side and the left side relative to the recessed portion 16, respectively, and horizontally extend from the recessed portion 16 to upper edges of the right side wall 29R and the left side wall 29L, respectively.

As illustrated in FIGS. 1, 2, and 4, the housing 11 includes two ribs 26 that project downward from the second top wall section 13 and the middle top wall section 14. The two ribs 26 are opposite each other. The ribs 26 project downward from border sections of the recessed portion 16 and the horizontal portions 17, respectively. As illustrated in FIG. 1, the ribs 26 extend linearly from the dividing wall 25 toward the discharge hole 24 and extends to the front wall 23. The ribs 26 extend from an opening edge of the through hole 27 to the short side opening edges of the discharge hole 24, respectively. The ribs 26 have projected ends 26A (lower ends) and end surfaces of the projected ends 26A are on a same plane. The rib 26 includes a rear section that projects from the middle top wall section 14 and the projection dimension of the rear section of the rib 26 gradually increases as it extends rearward and closer to the dividing wall 25.

As illustrated in FIGS. 1 and 4, the projected end surfaces of the projected ends 26A of the ribs 26 are contacted with a left edge section 411B of the upper surface 411U of the first board 411 and a right edge section 412B of the upper surface 412U of the second board 412, respectively. The board member 41 is mounted on the projected ends 26A of the ribs 26. According to such a configuration, as illustrated in FIG. 1, a space S is defined in the front section R1. The space S is defined by the board member 41 including the first board 411 and the second board 412, the ribs 26 (cavity side walls), and the middle top wall section 14 (a cavity upper wall section) and the second top wall section 13 (the cavity upper wall section) of the top wall 12. The space S is continuous to the through hole 27 and the discharge hole 24. The cooling fan device 30 is arranged in the housing 11 such that an outlet 31 of the cooling fan device 30 is opposite the through hole 27. Therefore, air fed through the outlet 31 by the cooling fan device 30 flows through the through hole 27 into the space S and is less likely to flow into other space than the space S.

The discharge hole 24 has a height measuring in the Z-direction that is equal to or greater than the projection dimension of the rib 26 projecting from the second top wall section 13. As illustrated in FIG. 1, the board member 41 is disposed at a same level as the lower long opening edges of the through hole 27 and the discharge hole 24. With such a configuration, the air is fed into the space S through the through hole 27 and discharged through the discharge hole 24 effectively and is less likely to be fed other space than the space S. The air is effectively fed through and discharged from the cavity 28.

Figure 7:
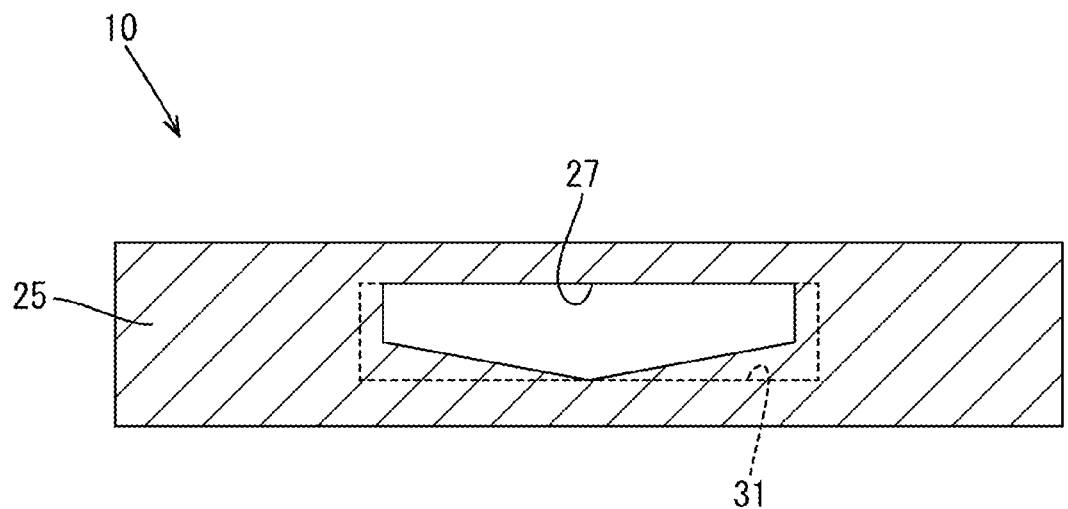
FIG. 7 is a cross-sectional view of the deep ultraviolet light emitting device along line VII-VII in FIG. 3.

As illustrated in FIGS. 1 and 4, the through hole 27 extends through the dividing wall 25 in the front-rear direction. The inner space of the front section R1 is connected to the inner space of the rear section R2 through the through hole 27. The through hole 27 has an opening dimension that is smaller than an opening dimension of the outlet 31 of the cooling fan device 30. As illustrated in FIG. 7, the opening edge of the through hole 27 is entirely within the opening edge of the outlet 31 seen from the front side. The dividing wall 25 and the side wall of the cooling fan device 30 are arranged in the Y-axis direction (a first arrangement direction) so as to be opposite each other and an entire opening edge of the through hole 27 is included in the opening edge of the outlet 31 with respect to the Y-axis direction (the first arrangement direction). According to such a configuration, the air fed from the cooling fan device 30 through the outlet 31 flows through the entire opening of the through hole 27.

Next, the flow of air within the deep ultraviolet light emitting device 10 will be described. When a fan of the cooling fan device 30 is operated, air is suctioned through the intake hole 22 and fed into a lower space of the rear section R2 (below the cooling fan device 30). Then, the air in the rear section R2 is suctioned into the cooling fan device 30 from a lower section of the cooling fan device 30 and fed toward the front section R1 through the outlet 31. The air fed from the cooling fan device 30 through the outlet 31 flows into the front section R1 of the housing 11 through the through hole 27. As illustrated in FIGS. 1 and 4, the air flowing into the front section R1 flows through the space S and is discharged outside the housing 11 through the discharge hole 24. The space S is defined by the upper surface 411U of the first board 411, the upper surface 412U of the second board 412, inner surfaces 261 of the ribs 26, lower surfaces 14L, 13L of the middle top wall section 14 and the second top wall section 13. The air flows into the space S through the outlet 31 of the cooling fan device 30 and the through hole 27 and discharged through the discharge hole 24. The board member 41, the ribs 26, and the middle top wall section 14 and the second top wall section 13 of the top wall 12 defines the space S and also defines a cavity 28 in which the air flows.

The width of the discharge hole 24 measuring in the longitudinal direction is equal to or greater than the width L1 of the board member 41 including the first board 411 and the second board 412. The height of the discharge hole 24 measuring in a vertical direction is equal to or greater than the projection dimension of the rib 26 measuring from the second top wall section 13. A front space S1 that is continuous to the discharge hole 24 is defined in the space S. The front space S1 is defined by the second top wall section 13, the ribs 26, and the board member 41 including the first board 411 and the second board 412. The opening size and the opening shape of the discharge hole 24 corresponds to the size and the shape of the front space S1 that is defined by the second top wall section 13, the ribs 26, and the board member 41 including the first board 411 and the second board 412. Specifically, the board member 41 is on a same level as the lower long opening edge of the discharge hole 24. The space below the board member 41 does not communicated with the discharge hole 24.

As illustrated in FIG. 1, the lower surface 13L of the second top wall section 13, the upper surface 411U of the first board 411, and the upper surface 412U of the second board 412 that define the front space S1 near the discharge hole 24 are flat surfaces without having any projections. The flat surfaces are smoothly connected to the opening edges of the discharge hole 24 without having any steps. According to such a configuration, the air that is fed into the space S through the through hole 27 and fed to the front space S1 does not hit the front wall 23 near the discharge hole 24. Therefore, the air flow within the front space S1 keeps its flowing speed and the air is discharged through the discharge hole 24 smoothly. Thus, the air flow created by the cooling fan device 30 keeps its high flowing speed and effectively cools down the upper surfaces 411U, 412U of the first board 411 and the second board 412. Thus, the first board 411 and the second board 412 are cooled down effectively.

A front portion of the cavity 28 defines the front space S1 and is defined by the second top wall section 13, the two ribs 26, and the board member 41 including the first board 411 and the second board 412. A vertical cross-sectional area of the front portion of the cavity 28 is preferably from 0.1 to 1.5 times of an opening area of the through hole 27. The middle top wall section 14 is tilted downward with respect to the horizontal direction and extends from the first top wall section 15 toward the discharge hole 24 and a space of the cavity 28 defined by the ribs 26, the board member 41, and the middle top wall section 14 is decreased toward the front portion of the cavity 28. With such a configuration, when the air that is fed through the through hole 27 into the space S flows toward the front space S1, the air is pressured by the lower surface of the middle top wall section 14 that is tilted downward. If the cross-sectional area of the front portion of the cavity 28 that defines the front space S1 is less than 0.1 times of the opening area of the through hole 27, the air resistance of the air that is pressured by the lower surface of the middle top wall section 14 is increased too much and this may cause backflow. If the cross-sectional area of the front portion of the cavity 28 is greater than 1.5 times of the opening area of the through hole 27, the air is not effectively pressured in the front space S1 and the flowing speed of the air flow is not increased.

A method of using the deep ultraviolet light emitting device 10 and operations of the deep ultraviolet light emitting device 10 will be described. The deep ultraviolet light emitting device 10 may be used for removing virus from the compartment of a vehicle 50 such as a taxi. As illustrated in FIGS. 5 and 6, the deep ultraviolet light emitting device 10 is mounted on a ceiling 51 of the vehicle 50 above a rear seat. The deep ultraviolet light emitting device 10 is mounted on the ceiling 51 of the vehicle 50 such that the cooling fan device 30 is on the vehicular rear side and the light emitter 40 is on the vehicular front side within the housing 11. The deep ultraviolet light emitting device 10 is mounted on the ceiling 51 such that the first board 411 and the second board 412 are arranged in the vehicular width direction. The deep ultraviolet light emitting device 10 may be fixed to the ceiling 51 when a vehicle is produced or may be detachably fixed to the ceiling 51. Specifically, the deep ultraviolet light emitting device 10 may be fixed to the ceiling 51 with a mounting member such as clips or screws.

When the deep ultraviolet light emitting device 10 is used, the first LED 421 and the second LED 422 emit deep ultraviolet light through the top surfaces toward the seats and the vehicular inner side surfaces (a door trim) at the angle of orientation of 120 degrees. As illustrated in FIG. 6, the top surface of each of the first LED 421 and the second LED 422 is tilted at 15 degrees with respect to the horizontal direction and faces the vehicular exterior side in the vehicular width direction, since each of the first board 411 and the second board 412 is tilted at 15 degrees with respect to the horizontal direction. According to such a configuration, the deep ultraviolet light can be supplied to a larger area including the seats and upper portions of the vehicular side surfaces compared to a configuration including the LEDs that face straight downward. Therefore, the operation of removing viruses can be performed for the large area in this embodiment. Namely, viruses can be removed from the large area including the seats and upper edge portions of the door trims that are likely and often touched by passengers. The irradiation of the deep ultraviolet light may be performed in a storehouse after transportation or may be performed while the vehicle is not in service or the driver is waiting for passengers.

Next, operations and advantageous effects of this embodiment will be described. The deep ultraviolet light emitting device 10 of this embodiment is to be mounted on the ceiling 51 of the vehicle 50. The deep ultraviolet light emitting device 10 includes the light emitter 40, the cooling fan device 30 for cooling the light emitter 40, and the housing 11 in which the light emitter 40 and the cooling fan device 30 are arranged. The light emitter 40 includes the board member 41, the first LED 421, and the second LED 422. The board member 41 is opposite the ceiling 51 and includes the first board 411 and the second board 412. The first LED 421 is mounted on the lower surface 411L of the first board 411 and the second LED 422 is mounted on the lower surface 412L of the second board 412. The housing 11 includes the intake hole 22 and the discharge hole 24.

When the deep ultraviolet light emitting device 10 is mounted on the ceiling 51, the light emitter 40 and the cooling fan device 30 are arranged laterally next to each other in the housing 11. The light emitter 40 and the cooling fan device 30 are arranged along the surface of the ceiling 51. The upper surface of the board member 41 is a portion of the cavity 28 that extends from the outlet 31 of the cooling fan device 30 to the discharge hole 24. The upper surface 411U of the first board 411 and the upper surface 412U of the second board 412 are portions of the cavity 28.

Since the light emitter 40 and the cooling fan device 30 are arranged laterally next to each other in an extending direction in which the cavity 28 extends (the first arrangement direction), the deep ultraviolet light emitting device 10 can be reduced in thickness compared to the configuration that the light emitter and the cooling fan device are vertically arranged and the cooling fan device is disposed on the light emitter. Since the upper surface of the board member 41 is configured as a portion of the cavity 28, the board member 41 can be cooled down effectively.

The extending directions of the first board 411 and the second board 412 that are perpendicular to the extending direction of the cavity 28 cross. The connection edges 411A, 412A of the first board 411 and the second board 412 are connected and extend along the cavity 28. The connection edges 411A, 412A of the first board 411 and the second board 412 are at a different level from opposite side edges of the first board 411 and the second board 412 that are opposite side edges of the connection edges 411A, 412A. The first board 411 and the second board 412 form an angle at the connection edges 411A, 412A. The first LED 421 and the second LED 422 are arranged such that the top surfaces, which are light emitting surfaces, face different directions. According to such a configuration, the area that is irradiated with the light of the first LED 421 and the second LED 422 is increased in the lateral direction compared to the configuration including two LEDs that face one direction. Therefore, the large area within the vehicular compartment can be irradiated with the light from the first LED 421 and the second LED 422.

The first board 411 and the second board 412 are arranged next to each other in the direction (the vehicular width direction) that crosses the extending direction in which the cavity 28 extends (the vehicular front-rear direction). The first board 411 and the second board 412 are tilted to have an angle therebetween. If two boards are arranged next to each other in the extending direction in which the cavity 28 extends and are tilted to have an angle between the two boards, air that is fed from a cooling fan device hits against a back surface of one of the tilted two boards and this results in an irregular air flow. Compared to such a configuration, the air flows through the cavity 28 straight and stable and the flowing speed is stable in this embodiment. This improves the cooling efficiency. The first board 411 and the second board 412 are evenly cooled.

When being mounted on the ceiling 51 of the vehicle 50, the first board 411 and the second board 412 are arranged in the vehicular width direction. According to such a configuration, the upper edge portion of the door trim that is likely touched by passengers can be irradiated with the deep ultraviolet light to remove viruses.

The upper wall of the cavity 28, which is the lower surface 13L of the second top wall section 13, is opposite and extends parallel to the upper surface of the board member 41. According to such a configuration, a distance between the upper surface of the board member 41 and the lower surface 13L of the second top wall section 13 is constant in the front section of the cavity 28. Accordingly, the air flow is stable and the cooling efficiency is further improved. The first board 411 and the second board 412 are cooled more evenly.

Other Embodiments

The present disclosure is not limited to the embodiment described above and illustrated in the drawings. The following embodiments may be included in the technical scope of the technology described herein. The technology described herein may be modified within the technical scope.

(1) The board member 41 may not include two separate boards but may be one plate member that is bent to include a first board section and a second board section on which a first LED and a second LED are mounted, respectively.

(2) The first board and the second board may be arranged next to each other laterally such that a joint section of the first board and the second board projects upward. Namely, a middle section of the board member in the right-left direction projects upward. With such a configuration, the area that is irradiated with the light from the first LED and the second LED with respect to the lateral direction can be increased.

Figure 8:
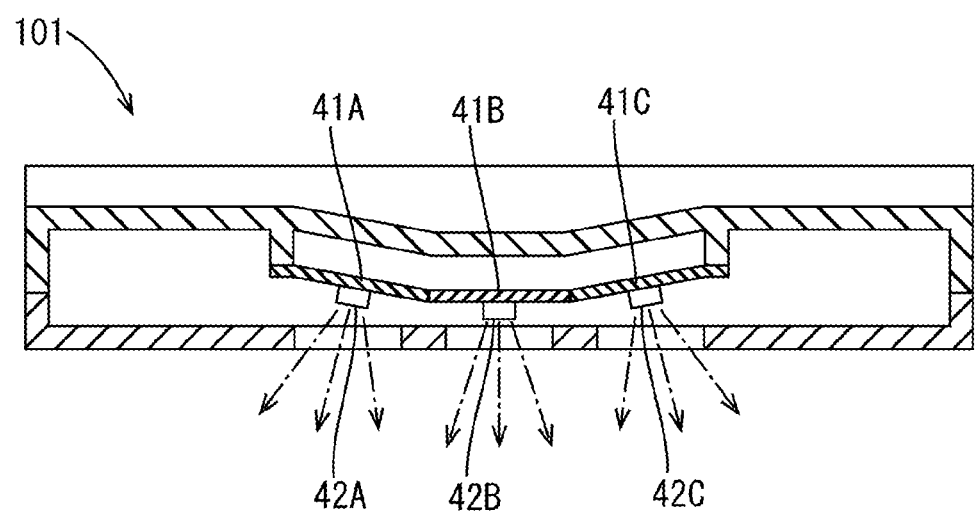
FIG. 8 is a cross-sectional view of a deep ultraviolet light emitting device according to another embodiment.

(3) As illustrated in FIG. 8, a deep ultraviolet light emitting device 101 may include a board member including three boards 41A, 41B, 41C that are arranged to have an angle between adjacent two boards out of the three boards 41A, 41B, 41C. LEDs 42A, 42B, 42C are mounted on the respective boards 41A, 41B, 41C.

(4) The first board and the second board may be arranged in the extending direction in which the cavity extends (the vehicular front-rear direction).

(5) The angle of orientation of light emitted by the LED is not limited to the one described in the present embodiment but may be defined as appropriate. A deep ultraviolet light emitting device may include a device for changing the angle of orientation of light.

(6) The height of the housing 11 is smaller in the front section than in the rear section in the present embodiment. However, the housing may have a constant height as a whole.

(7) The lower surface of the second top wall section 13 may not necessarily extend parallel to the upper surface of the board member 41.

(8) The direction of the deep ultraviolet light emitting device 10 that is mounted on the ceiling 51 is not limited to the one described in the present embodiment.

(9) The deep ultraviolet light emitting device 10 may be mounted on any other portions of the vehicular compartment such as an inner side wall and a floor.

The invention claimed is:

1. A light emitting device that is to be mounted on a mount surface of a vehicular compartment, the light emitting device comprising:
   a housing having a box shape and including a first section that has an air intake hole and a second section that has an air discharge hole and includes a discharge cavity having the discharge hole;
   a cooling fan device arranged in the first section; and
   a light emitter arranged in the second section and arranged next to the cooling fan device in a first arrangement direction and laterally along the mount surface, the light emitter including
   a board member having a first surface that is opposite the mount surface of the vehicular compartment and a second surface that is an opposite surface of the first surface, the first surface being defined as a portion of the discharge cavity, and
   a first light emitting element mounted on the second surface of the board member.

2. The light emitting device according to claim 1, wherein the light emitter further includes a second light emitting element, the board member includes a first board section on which the first light emitting element is mounted and a second board section on which the second light emitting element is mounted, and the first board section and the second board section form an angle between the first board section and the second board section.

3. The light emitting device according to claim 2, wherein the first board section and the second board section are next to each other in a second arrangement direction that cross the first arrangement direction.

4. The light emitting device according to claim 2, wherein the first board section and the second board section are arranged in a width direction of a vehicle.

5. The light emitting device according to claim 2, wherein
the first board section has a first connection edge and the second board section has a second connection edge that is connected to the first connection edge, and the first board section and the second board section form an angle at the first connection edge and the second connection edge.

\* \* \* \* \*